United States Patent
Keller

(10) Patent No.: US 7,591,855 B2
(45) Date of Patent: Sep. 22, 2009

(54) KNEE PROSTHESIS WITH ROTATION BEARING

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 695 days.

(21) Appl. No.: 10/474,952

(22) PCT Filed: Apr. 15, 2002

(86) PCT No.: PCT/EP02/04157

§ 371 (c)(1),
(2), (4) Date: May 10, 2004

(87) PCT Pub. No.: WO02/085258

PCT Pub. Date: Oct. 31, 2002

(65) Prior Publication Data

US 2004/0186583 A1    Sep. 23, 2004

(30) Foreign Application Priority Data

Apr. 25, 2001 (EP) .................................. 01110260

(51) Int. Cl.
*A61F 2/38* (2006.01)
(52) U.S. Cl. ................. 623/20.24; 623/20.29
(58) Field of Classification Search ... 623/20.21–20.29, 623/20.14, 20.15
See application file for complete search history.

(56) References Cited

U.S. PATENT DOCUMENTS

| | | | | |
|---|---|---|---|---|
| 4,136,405 A | * | 1/1979 | Pastrick et al. | ........... 623/20.25 |
| 4,219,893 A | * | 9/1980 | Noiles | ...................... 623/20.25 |
| 4,790,853 A | * | 12/1988 | Engelbrecht et al. | ...... 623/20.25 |
| 5,411,555 A | | 5/1995 | Nieder | |
| 6,090,144 A | * | 7/2000 | Letot et al. | ................ 623/20.34 |
| 6,099,570 A | * | 8/2000 | Livet et al. | ................ 623/20.21 |
| 6,413,279 B1 | * | 7/2002 | Metzger et al. | ........... 623/20.29 |

FOREIGN PATENT DOCUMENTS

| | | |
|---|---|---|
| DE | 26 36 816 A1 | 2/1977 |
| DE | 27 447 10 C2 | 4/1979 |
| EP | 0 539 654 B1 | 5/1993 |
| EP | 0 913 132 A1 | 5/1999 |
| EP | 0913132 A1 * | 5/1999 |
| EP | 1 108 403 A1 | 6/2001 |
| JP | 5-168655 | 7/1993 |
| JP | 52-23893 | 9/1993 |

OTHER PUBLICATIONS

English Translation of International Preliminary Examination Report for PCT/EP02/04157 dated Jul. 7, 2003.

* cited by examiner

*Primary Examiner*—William H. Matthews
(74) *Attorney, Agent, or Firm*—Morrison & Foerster LLP

(57) ABSTRACT

A knee prosthesis including a femoral component, a tibial component and an intermediate piece which connects these forming a flexion bearing with the femoral component and a rotation bearing with the tibial component, which rotation bearing can be locked relative to the tibial part. To allow the physician to decide during the operation whether to use a rotation-free prosthesis or a rotationally fixed prosthesis, the intermediate piece is alternatively provided with a projection which engages in a matching recess in the tibial component.

9 Claims, 2 Drawing Sheets

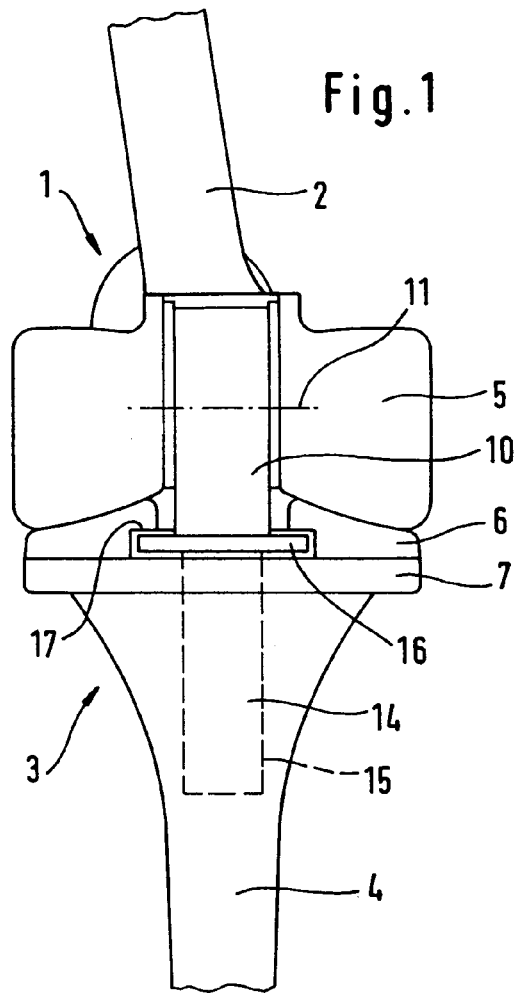
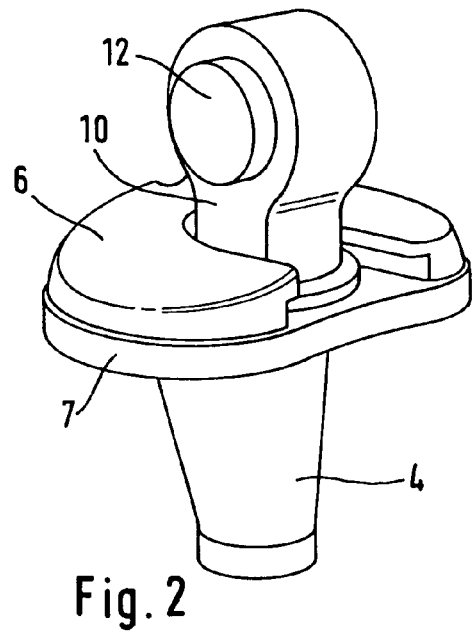
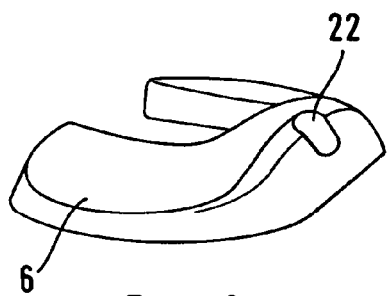
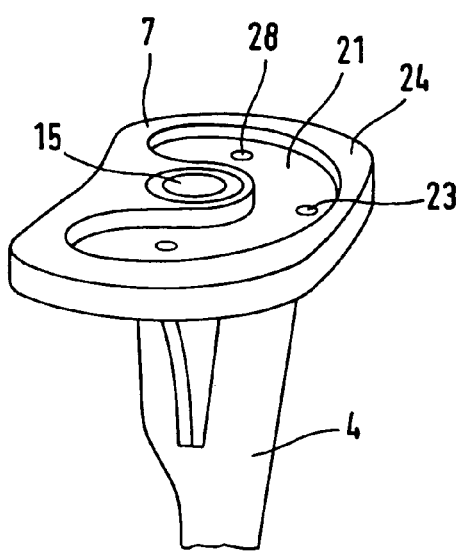
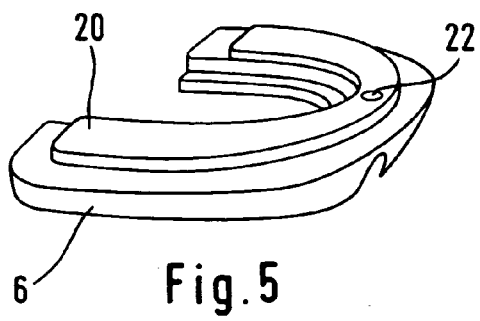

KNEE PROSTHESIS WITH ROTATION BEARING

FIELD AND BACKGROUND OF THE INVENTION

The poorer the state of preservation of the ligament apparatus of a knee which is to be provided with a knee prosthesis, the greater inherent stability demanded of the prosthesis. If it is a ligament apparatus of reduced stability, it may be necessary to use a prosthesis type in which the relative movement between femoral component and tibial component is limited by a stabilizing intermediate part to the flexion movement about a horizontal transverse axis and to a rotation movement about an axis substantially parallel to the tibia (DE-C-2 744 710). For this, it is required that the ligament apparatus can at least still control the rotation movements. If this ability too has been lost, the rotation movement must be excluded and the degree of freedom of the prosthesis must be limited to the flexion movement. Different prosthesis structures are normally used for these two cases of application. If the decision whether to choose a rotation-free or rotationally fixed prosthesis is to be made only during the operation, a prosthesis system can be used whose components are partly exchangeable (EP-B-539 654), with one matching femoral component and different tibial components being provided. Finally, it has also already been proposed (DE-A-2 636 816) to use for both cases a rotation-free prosthesis in which a fixing device can be arranged which excludes the rotation movement if so desired. This is intended to be done by drilling a hole through the bone and the rotation bearing after implantation and then introducing a fixing pin into the hole to prevent turning of the rotation bearing. This is obviously impracticable. Instead, a fixing pin can also be guided exclusively inside the prosthesis through a rotation axial bearing and prevent its turning. It has not been disclosed whether this proposal has ever been adopted in practice. In fact, there are a great many practical difficulties against it. One factor may have been that, compared to a prosthesis which exclusively includes a flexion hinge, it is relatively expensive to use a prosthesis additionally provided with a rotation bearing and then to lock this.

SUMMARY OF THE INVENTION

Nevertheless, in endeavouring to make available a prosthesis which permits a simple intraoperative decision between the rotation-free and the rotationally fixed version, the invention follows on from the latter proposal and makes it suitable in practical terms by means of the features of the invention of this application. Accordingly, the intermediate part which connects the femoral component to the tibial component, and forms the rotation bearing with the tibial component, is provided with a projection which engages in a matching recess in the tibial component.

This concept is advantageously realized by the fact that the prosthesis system comprises an alternative intermediate part (or component of the intermediate part) with or without projection, this projection being connected permanently to the intermediate part (or the component of the intermediate part). Thus, after implantation both of the femoral component and of the tibial component, the physician is given the possibility, by alternative selection of the projection-carrying part, of making a decision in favour of one or other prosthesis version and possibly also of trying out both versions. Instead of this, it is also possible to equip the intermediate part (or its component) with a connecting device for alternative connection to the projection.

If the tibial component has a support plate with at least one depression for receiving a tibial plateau, the projection is expediently designed to cooperate with this depression. Since this depression is of sizeable design, it permits a very stable rotational connection. The tibial component can be used without any adjustment in both versions of the prosthesis. In this embodiment, the projection is expediently formed by a plate which fits into the depression and which in itself and/or with the borders of the depression forms cutouts for receiving parts of a tibial plateau.

BRIEF DESCRIPTION OF THE DRAWINGS

The invention is explained in more detail below with reference to the drawing which depicts an advantageous illustrative embodiment. In the drawing:

FIG. 1 shows a dorsal view of the prosthesis,

FIG. 2 shows a perspective view of the tibial component with the intermediate part, FIG. 3 shows a perspective top view of the tibial plateau, FIG. 4 shows a perspective view of the support plate of the tibial component, FIG. 5 shows a perspective bottom view of a normal tibial plateau.

DETAILED DESCRIPTION OF THE INVENTION

Figure 6:
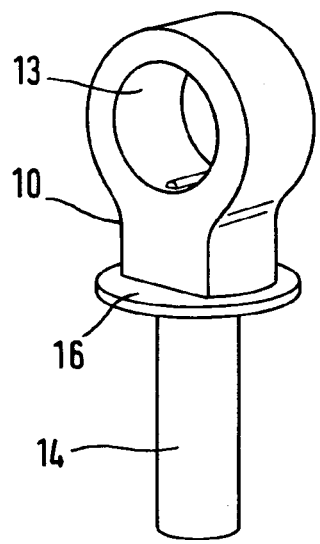
FIG. 6 shows a perspective view of a normal intermediate part.

The prosthesis has a femoral component 1 with a stem 2 intended for implantation in the femoral bone, and a tibial component with a stem 4 intended for implantation in the tibia. The femoral component has wing-like runners 5 lying on a tibial plateau 6 which promotes sliding and which is supported by a support plate 7 of the tibial component. To stabilize the two components relative to one another, an intermediate piece 10 is provided which, with the femoral component, forms a hinge indicated in FIG. 1 by an axis line 11. FIG. 2 shows an axis stump 12 which protrudes from the intermediate piece 10 and which cooperates with bearing bores (not shown) in the femoral component 1. It sits in a bore 13 of the intermediate part.

The intermediate piece 10 further forms a rotation bearing with the tibial component, namely by the rod 14 which is connected integrally to the intermediate part and which is mounted in a bearing bore 15 in the tibial component. The bearing bore 15 extends substantially parallel to the direction of the tibia which can be identified from the stem 4 of the prosthesis. The intermediate piece 10 thus limits the relative movement between the femoral component and tibial component to the flexion movement about the hinge axis 11 and to the rotation movement about the axis of the rotation bearing 14, 15. The intermediate piece 10 can also be equipped with a collar 16 which, by cooperating with a step 17 of the tibial plateau 6, prevents undesired lifting of the femoral component from the tibial component.

The tibial plateau 6 is made of polyethylene, for example, and on its upper side is shaped in a known manner in such a way that in the event of a rotation the femoral component is lifted slightly in relation to the tibial component, so that a restoring force is generated which seeks to return it to the neutral central position under the transmitted load.

The tibial plateau 6 is supported by the support plate 7 preferably over its entire surface. It has on the underside a horseshoe-shaped projection 20 whose height and contour are designed to match those of a horseshoe-shaped depression 21 in the support plate 7. The correct setting of the tibial plateau on the support plate is ensured by the interaction of the projection 20 and of the depression 21. By way of a screw hole 22 in the tibial plateau, the latter can be secured in the assembled position in the support plate by means of a screw (not shown) and a threaded bore 23. The support plate 7 is provided with threaded bores 28 and the locking plate 25 is provided at corresponding positions with screw holes 29 which allow the locking plate to be screwed rigidly to the tibial component.

Figure 7:
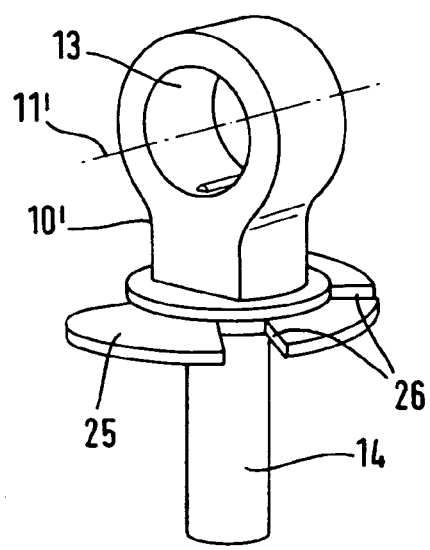
FIG. 7 shows a perspective view of an intermediate part which prevents rotation.
Figure 8:
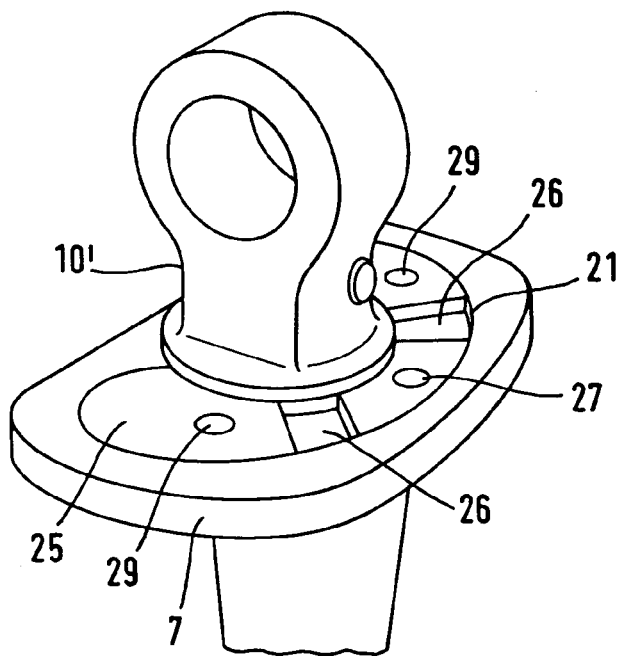
FIG. 8 shows a perspective view of the tibial component with a fitted intermediate part which inhibits rotation.
Figure 9:
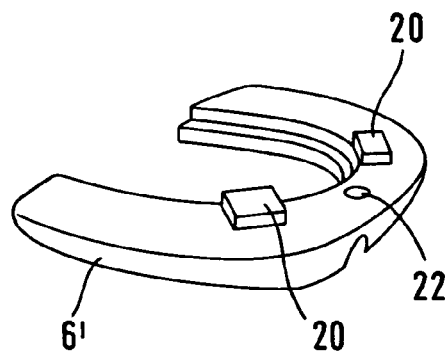
FIG. 9 shows a perspective bottom view of a tibial plateau to be used in connection with an intermediate part which prevents rotation.

The intermediate piece in the normal embodiment has the configuration shown in FIG. 6. Alternatively, the intermediate piece 10' according to FIG. 7 can be used which differs from the normal intermediate piece 10 in that it is connected rigidly to a locking plate 25 whose contour is an exact match of that of the depression 21 in the support plate 7. When the intermediate piece 10' is fitted into the tibial component 3, the locking plate 25 fills the depression 21 substantially completely. Its surface lies at the same height as the edge 24 of the support plate 7 surrounding the depression 21. This results in a continuously plane contact surface for the tibial plateau 6'. In order to secure the latter in the correct position, it is provided with projections 20' which take the place of the horseshoe-shaped projection 20 of the normal tibial plateau 6 and are designed to fit in cutouts 26 in the locking plate 25. In the assembled state, the projections 20' engage in the cutouts 26 and thereby secure the position of the tibial plateau. Moreover, like the normal tibial plateau, it can be secured on the threaded bore 23 of the support plate 7 by means of a screw passing through the bore 22 of the plateau and a bore 27 of the locking plate.

The locking plate 25 is secured on the intermediate piece 10' at such a height that the distance between the locking plate 25 and the hinge axis 11' of the intermediate piece exactly matches the position of the hinge axis 11 defined by the height of the runners 5 and of the plateau 6. In other words, the flexion axis 11 set by the runners 5 and the plateau 6 is intended to exactly correspond to the axis 11' of the intermediate part 10'. This is intended to ensure that most of the load is transmitted onwards via the large-area contact between runners 5 and the tibial plateau 6. If it is desired that no force be transmitted via the intermediate piece, the locking plate 25 is connected to the intermediate piece 10' not rigidly, but instead axially displaceably, although not pivotably. This can be done, for example, by providing the collar 16 with bores and by the locking plate 25 having pins which are parallel to the rod 4 and which are guided through these bores. The locking plate 25 can then move in the axial direction relative to the intermediate piece 10', but is connected to it in a rotationally fixed manner via the pins and bores.

Further details of the prosthesis configured according to the invention are to be found in the applications filed at the same time by the same Applicant and bearing the administrative file references: LINO515PEP and LINO516PEP.

The invention claimed is:

1. A knee prosthesis system, comprising:
   a femoral component comprising runners;
   a tibial component comprising a tibial plateau that is rotationally fixed relative to the tibial component, the runners being arranged to load-bearingly engage the tibial plateau;
   a first intermediate piece configured to connect the femoral component and the tibial component forming a flexion bearing with the femoral component and a rotation bearing with the tibial component, allowing the runners to rotate relative to the tibial plateau; and
   a second intermediate piece configured to connect the femoral component and the tibial component forming a flexion bearing with the femoral component and fully block rotation between the femoral component and the tibial component, blocking the runners from rotating relative to the tibial plateau;
   wherein the knee prosthesis system is configured to use either the first intermediate piece or the second intermediate piece to connect the femoral component and the tibial compoment.

2. The knee prosthesis system according to claim 1, wherein a projection of the second intermediate piece engages a matching recess in the tibial component so that the rotation bearing is fully blocked.

3. The knee prosthesis system according to claim 2, wherein the projection is permanently connected to the second intermediate piece.

4. The knee prosthesis system according to claim 3, wherein the tibial component comprises a support plate with at least one depression formed therein to receive the tibial plateau or parts of the tibial plateau, the projection being designed to cooperate with the at least one depression.

5. The knee prosthesis system according to claim 4, wherein the projection is formed by a plate which fits into the depression and which forms cutouts for receiving the parts of the tibial plateau.

6. The knee prosthesis system according to claim 4, wherein the projection is formed by a plate which fits into the depression and which in conjunction with borders of the depression forms cutouts for receiving the parts of the tibial plateau.

7. The knee prosthesis system according to claim 2, wherein the tibial component comprises a support plate with at least one depression formed therein to receive the tibial plateau or parts of the tibial plateau, the projection being designed to cooperate with the at least one depression.

8. The knee prosthesis system according to claim 7, wherein the projection is formed by a plate which fits into the depression and which forms cutouts for receiving the parts of the tibial plateau.

9. The knee prosthesis system according to claim 7, wherein the projection is formed by a plate which fits into the depression and which in conjunction with borders of the depression forms cutouts for receiving the parts of the tibial plateau.

\* \* \* \* \*